US012575592B2

(12) United States Patent
Lu et al.

(10) Patent No.: US 12,575,592 B2
(45) Date of Patent: Mar. 17, 2026

(54) METHOD FOR PRODUCING BIOMIMETIC NUTRIENT MIXTURE VIA BIOMIMICRY

(71) Applicant: AMBER NANOTECH CO., LTD, Hsinchu County (TW)

(72) Inventors: Lin Lu, Taoyuan City (TW); Chun-Lun Chiu, Taoyuan City (TW); Ching-Cheng Chen, Taoyuan City (TW); Tai-Jung Lai, Hsinchu County (TW); Tsu-Jun Lu, Hsinchu County (TW); Chung-Jung Hung, Tainan City (TW)

(73) Assignee: AMBER NANOTECH CO., LTD, Hsinchu County (TW)

( * ) Notice: Subject to any disclaimer, the term of this patent is extended or adjusted under 35 U.S.C. 154(b) by 568 days.

(21) Appl. No.: 17/983,588

(22) Filed: Nov. 9, 2022

(65) Prior Publication Data

US 2024/0049763 A1 Feb. 15, 2024

(30) Foreign Application Priority Data

Aug. 12, 2022 (TW) .................................. 111130508

(51) Int. Cl.
| | |
|---|---|
| *A23L 33/16* | (2016.01) |
| *A61K 8/23* | (2006.01) |
| *A61K 33/04* | (2006.01) |
| *C12P 3/00* | (2006.01) |

(52) U.S. Cl.
CPC ................ *A23L 33/16* (2016.08); *A61K 8/23* (2013.01); *C12P 3/00* (2013.01); *A61K 33/04* (2013.01)

(58) Field of Classification Search
CPC ......... A23L 33/16; A61K 36/00; A61K 33/04; A61K 8/23; C12P 3/00
See application file for complete search history.

(56) References Cited

U.S. PATENT DOCUMENTS 6,238,575 B1 * 5/2001 Patil ....................... A01N 25/34
210/764

FOREIGN PATENT DOCUMENTS

| | | | |
|---|---|---|---|
| CN | 101112999 A | * | 1/2008 |
| CN | 102925359 | | 2/2013 |
| CN | 102925359 A | * | 2/2013 |

OTHER PUBLICATIONS

Sampath et al (Journal of Biotechnology, 2022, vol. 360, pp. 92-109) (Year: 2022).*
Quattrini (Clinical Cases in Mineral and Bone Metabolism, 2016, vol. 13, pp. 173-180) (Year: 2016).*
EGLE (Algae—A Naturally Occurring Phenomenon, Revised 2022, Michigan.gov/EGLE) (Year: 2022).*
Wei et al (International Journal of Sediment Research, 2021, vol. 36, pp. 542-554) (Year: 2021).*
Singh (Bio-Nanoparticles, Wiley Blackwell, copyright 2015, pp. 1-333) (Year: 2015).*
Helman et al (OSU Oregon State University, Biomimetic Synthesis of GeO2 and TiO2 Utilizing the R5 and Poly-L-Lysine Peptides, Available in 2018, https://ir.library.oregonstate.edu/concern/undergraduate_thesis_or_projects/bz60cz05z). (Year: 2018).*
CN-102925359-A (Google English translation, downloaded May 2025) (Year: 2025).*
Helman et al (OSU Oregon State University, Biomimetic Synthesis of GeO2 and TiO2 Utilizing the R5 and Poly-L-Lysine Peptides, Available in 2018, https://ir.library.oregonstate.edu/concern/undergraduate_thesis_or_projects/bz60cz05z) (showing date of availability is 2018) (Year: 2018).*
CN-101112999-A (Google English translation, downloaded Oct. 2025) (Year: 2025).*
Zinicovscaia et al (Ecol Chem Eng S, 2016, vol. 23, pp. 559-569) (Year: 2016).*
Morsy et al (Universal Journal of Microbiology Research, 2014, vol. 2, pp. 36-43) (Year: 2014).*
Wikipedia, Hoagland solution, Internet source <URL: https://en.wikipedia.org/wiki/Hoagland_solution>.
Qin Baoli et al., Effects of sodium selenite on growth and antioxidant enzyme activity of green alga *Chlorella pyrenoidosa*, Dec. 2020, Journal of Dalian Ocean University.
Wang Jing, The effect of the metal nanoparticles (Fe / Ni) on growth in alga *Chlorella pyrenoidosa*, Oct. 2011, Journal of Dalian Ocean University.

* cited by examiner

*Primary Examiner* — Mark V Stevens
(74) *Attorney, Agent, or Firm* — WPAT, PC

(57) ABSTRACT

Provided is a method for producing a biomimetic nutrient mixture via biomimicry, comprising: Step (1) providing a mineral nutrient element precursor solution, and Step (2) reacting the mineral nutrient element precursor solution with a natural bio-reactor to obtain the biomimetic nutrient mixture, wherein the biomimetic nutrient mixture comprises a mineral nutrient element and a nutrient solution. The method can produce high biologically active mineral nutrient by an auto-synthesizing natural antioxidant through photosynthesis in the natural bio-reactor containing chlorophyll, which can provide mineral nutrient element without additional extraction procedure or extra component for manufacturing a nutritional supplement.

12 Claims, 5 Drawing Sheets

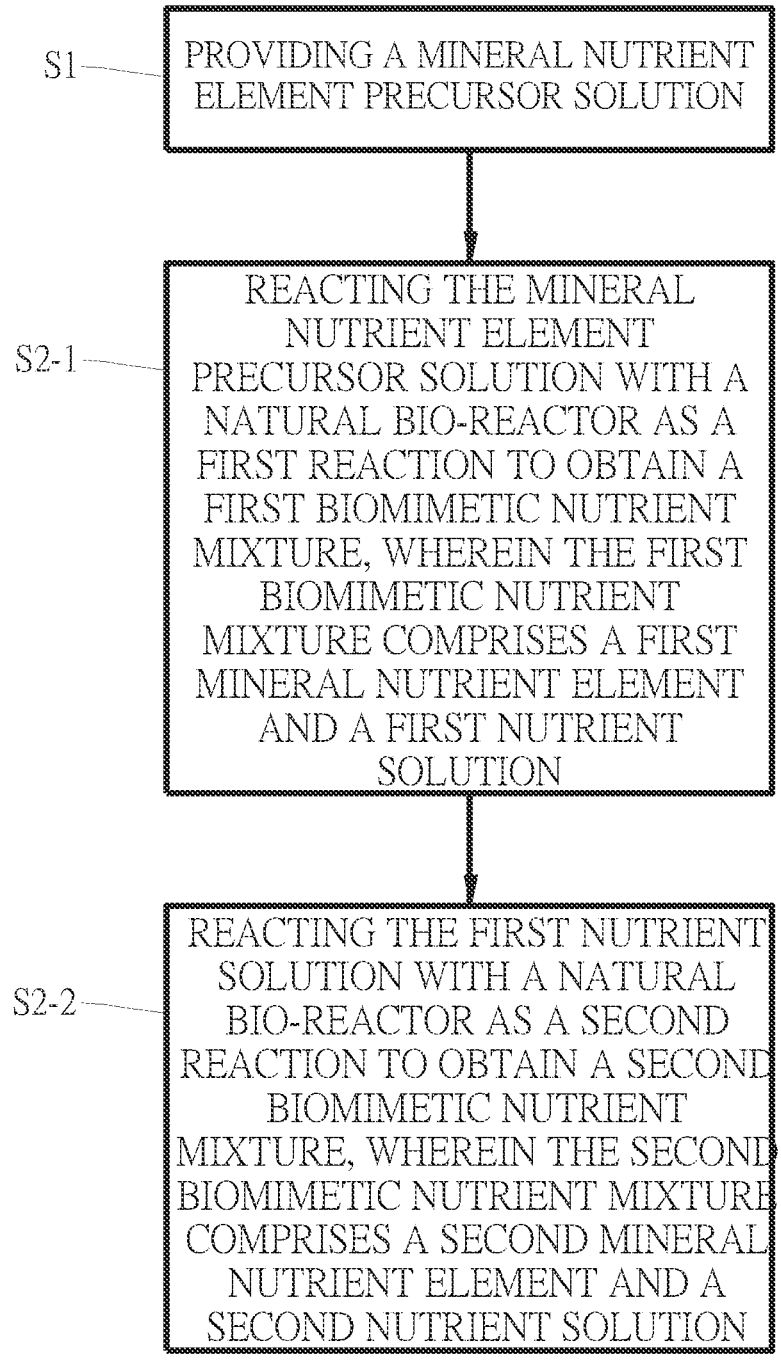

S1 — PROVIDING A MINERAL NUTRIENT ELEMENT PRECURSOR SOLUTION

S2-1 — REACTING THE MINERAL NUTRIENT ELEMENT PRECURSOR SOLUTION WITH A NATURAL BIO-REACTOR AS A FIRST REACTION TO OBTAIN A FIRST BIOMIMETIC NUTRIENT MIXTURE, WHEREIN THE FIRST BIOMIMETIC NUTRIENT MIXTURE COMPRISES A FIRST MINERAL NUTRIENT ELEMENT AND A FIRST NUTRIENT SOLUTION

S2-2 — REACTING THE FIRST NUTRIENT SOLUTION WITH A NATURAL BIO-REACTOR AS A SECOND REACTION TO OBTAIN A SECOND BIOMIMETIC NUTRIENT MIXTURE, WHEREIN THE SECOND BIOMIMETIC NUTRIENT MIXTURE COMPRISES A SECOND MINERAL NUTRIENT ELEMENT AND A SECOND NUTRIENT SOLUTION

FIG.2

METHOD FOR PRODUCING BIOMIMETIC NUTRIENT MIXTURE VIA BIOMIMICRY

CROSS REFERENCE

Pursuant to 35 U.S.C. § 119(a), this application claims the benefit of the priority to Taiwan Patent Application No. 111130508, filed on Aug. 12, 2022. The content of the prior application is incorporated herein by its entirety.

BACKGROUND OF THE INVENTION

1. Field of the Invention

The present invention relates to a method for producing a nutrient element mixture, and particularly to a method for producing a nutrient element mixture comprising the nutrient element required for organism growth.

2. Description of the Prior Arts

Nutrient elements refer to substances obtained from food, which promote growth and development, maintain health, and repair body tissues in the human body. That is to say, they are substances that provide nutrient to organisms. Generally, the nutrient elements can be divided into two groups, the nutrient elements for producing energy (so called the nutrient elements for providing energy or macronutrients) and the micronutrients. The macronutrients comprise carbohydrates, fats, and proteins. The micronutrients are nutrient substances that are needed by the organisms in very small amounts but are critical for maintaining normal physiological function of the organisms.

In recent years, crop production and management modes have become more and more suitable for the health maintenance strategy of the human body. By supplementing nutritional supplements such as vitamins, glucose, amino acids, the nutritional supplements not only provide the energy for regulating metabolism balance, but also enhances the body's resistance to the damages caused by pathogens and drugs. Therefore, plants also need to be supplied with nutrients to regulate metabolism balance, enhance resistance, and recover to normal growth.

Take plants as an example: in the 1920s, D. R. Hoagland (Dr. Hoagland) was a pioneer in the study of plant mineral nutrition. Currently, some commercial or research culture media are mostly modified from the Hoagland formulation (Hoagland, D. R.; Snyder, W. C. (1933). "Nutrition of strawberry plant under controlled conditions. (a) Effects of deficiencies of boron and certain other elements, (b) susceptibility to injury from sodium salts". Proceedings of the American Society for Horticultural Science. 30:288-294). In 1972, Epstein determined whether an element is an essential element based on two principles. First, whether this element is necessary for growth and development of a plant. That is, a plant cannot complete its normal life cycle under deficiency of this element. For example, while lacking certain element, a plant is not able to produce normal seeds. Second, this element is a component constructing the plant or a metabolic component of the plant.

According to the aforementioned two principles (meeting one or two requirements), there are 17 elements that are essential elements for the growth of higher plants: hydrogen (H), carbon (C), oxygen (O), nitrogen (N), potassium (K), calcium (Ca), magnesium (Mg), phosphorus (P), sulfur(S), chlorine (Cl), boron (B), iron (Fe), manganese (Mn), zinc (Zn), copper (Cu), nickel (Ni), molybdenum (Mo), etc.

Besides, other than the 17 essential elements, some other elements are required to add into the medium for certain plants. The additionally added mineral elements are called beneficial elements. The currently clearly identified beneficial elements are sodium (Na), silicon (Si), selenium (Se), cobalt (Co), and so on.

The composition of the nutrition supplement comprises chemical synthetic substances, natural extracts or a mixture of both. The functions of the nutrition supplement are mainly for promoting crop's quality and yield, and increasing resistance to diseases, pests, or stress by meeting the nutritional needs of different species of crops and different physiological stages. The common application methods are mainly soaking, smearing, spraying or watering.

However, it may need to go through certain processing procedures to produce the nutritional supplement, and therefore may cause some disadvantages as follows. First, the nutrition components may be destroyed by the mechanical force or temperature during refinement or extraction processing. Second, it is required to add accessory ingredients to stabilize or protect the main components of the nutritional supplement. Besides, the extraction process is complicated, the required equipment and solvents are expensive, several destructive processes destroy the natural antioxidants, which makes the natural antioxidants lose their anti-oxidative ability, the continuously production process is inapplicable, etc., so that the economic value is low. On the other hand, the advanced supercritical extraction method also has the following disadvantages: the equipment is expensive, the extraction ability to polar substances is weak, additional solubilizers are required to increase the extraction rate, high pressure is required during extraction, energy consumption is large, and samples must be frozen and dried before extraction to reduce interfering substances. Therefore, it is necessary to develop a method to provide mineral nutrition being beneficial for organism growth without an extraction process and without addition of accessory ingredients.

SUMMARY OF THE INVENTION

In light of the deficiency of the current technology, the purpose of the present invention is to provide a method for providing mineral nutrition which is beneficial for organism growth without an extraction process and without addition of accessory ingredients.

To achieve the above purpose, the present invention provides a method for producing a biomimetic nutrient mixture via biomimicry, comprising:

Step (1) providing a mineral nutrient element precursor solution, wherein the mineral nutrient element precursor solution comprises metallic salt and metalloid salt, the metallic salt is a salt of Mg, aluminium (Al), Ca, titanium (Ti), Cu, gold (Au), Fe, platinum (Pt), ruthenium (Ru), rhodium (Rh), palladium (Pd) or silver (Ag), and the metalloid salt is a salt of Se or Germanium (Ge); and Step (2) reacting the mineral nutrient element precursor solution with a natural bio-reactor to obtain the biomimetic nutrient mixture, wherein the natural bio-reactor is an organism comprising chlorophyll, and the organism comprising chlorophyll is a Cyanophyta-bacteria belonging to Kingdom Monera or an alga belonging to Kingdom Protista, and the biomimetic nutrient mixture comprises a mineral nutrient element and a nutrient solution.

By means of fully mixing the salt solution and the natural bio-reactor comprising chlorophyll for reacting, the natural bio-reactor auto-synthesizes natural anti-oxidative components (such as glucose) or other products of related reactions caused by photosynthetic electron transport chain (for example, flavonoids, indole, polysaccharides, phycobiliproteins, etc.) which can be used as a reducing agent. In the meantime, the salt compound goes through reduction reaction under room temperature to produce the mineral nutrient element having high biological activity, for example, the mineral nutrient element has high anti-oxidative activity, so it can be used to scavenge free radicals. The aforementioned mineral nutrient elements comprise reduced metal or reduced metalloid. The preparation of the mineral nutrient element having high biological activity by auto-synthesizing the anti-oxidative component through photosynthesis is an embodiment of Biomimicry.

According to the present invention, "the mineral nutrient element precursor solution reacts with a natural bio-reactor" refers to mixing the mineral nutrient element precursor solution and the natural bio-reactor, which makes the natural bio-reactor immersed in the mineral nutrient element precursor solution so as to react with the mineral nutrient element precursor solution.

According to the present invention, there is no specific limitation on the mineral nutrient element precursor comprised in the mineral nutrient element precursor solution. As long as the mineral nutrient element precursor dissolves in water to form the mineral nutrient element precursor solution, said mineral nutrient element precursor is applicable in the present invention. In some embodiment of the present invention, the mineral nutrient element precursor solution of Cu, Au, Zn, Ag or Se is used to produce biomimetic nutrient mixture comprising Cu. Au, Zn. Ag or Se, respectively. Among them, the metallic salt or metalloid salt comprises normal salt, acid salt, alkali salts, complex salt, double salt, or any combination thereof. Besides, the mineral nutrient element precursor may comprise the oxide of the mineral nutrient element.

For example, the mineral nutrient element precursor is selenium salt, which comprises selenium oxide, selenium halide, selenium ion, selenious acid, selenite ion, selenate ion, selenosulfate ion, but it is not limited thereto. Specifically, the selenium halide may be represented as $Se_mX_n$, wherein X is F. Cl or Br; m is an integer 1 or 2; and n is an integer 1, 2, 3 or 4. Preferably, the selenium halide may be selenium difluoride ($SeF_2$), selenium dichloride ($SeCl_2$), selenium dibromide ($SeBr_2$), diselenium dichloride ($Se_2Cl_2$), or selenium tetrachloride ($SeCl_4$). Specifically, the selenium ion may be derived from a selenium halide, but it is not limited thereto. The selenite ion may be derived from sodium selenite ($Na_2SeO_3$), the selenious acid, or potassium selenite ($K_2SeO_3$), but it is not limited thereto. The selenate ion may be derived from sodium selenate ($Na_2SeO_4$) or potassium selenate ($K_2SeO_4$), but it is not limited thereto. The selenosulfate ion may be derived from sodium selenosulfate ($Na_2SeSO_3$), but it is not limited thereto. Accordingly, the mineral nutrient element precursor solution containing the selenium precursor may contain some ions besides those derived from the selenium precursor, such as halogen ions or alkali metal cations, but it is not limited thereto.

According to the present invention, the mineral nutrient element is a metal element or a metalloid element. Preferably, the metal element or metalloid element is in an elemental state.

Preferably, a molar concentration of the mineral nutrient element precursor solution is 0.05 M to 1.0 M. More preferably, a molar concentration of the mineral nutrient element precursor solution is 0.08 M to 1.0 M.

Preferably, a molar concentration of the mineral nutrient element in a mixture obtained by mixing the mineral nutrient element precursor solution and the natural bio-reactor is 1.25 mM to 6.25 mM. Preferably, a molar concentration of the mineral nutrient element in a mixture obtained by mixing the mineral nutrient element precursor solution and the natural bio-reactor is 2 mM to 4 mM.

A weight ratio of the mineral nutrient element precursor in the mineral nutrient element precursor solution and the natural bio-reactor is from 1:1 to 1:10000. For example, the weight ratio can be 1:400 to 1:1500, or 1:500, 1:600, 1:700, 1:1100, 1:1200, 1:1300 or 1:1400.

According to the present invention, the natural bio-reactor can auto-synthesize the natural anti-oxidative component through photosynthesis. The natural anti-oxidative component is a necessary reducing agent for synthesizing the mineral nutrient element, which reduces the mineral nutrient element precursor to produce colloidal particles comprising the metal or metalloid.

Preferably, the natural bio-reactor for example can be selected from Cyanophyta-bacteria belonging to Kingdom Monera such as Cyanobacteria (also known as blue-green algae) or Chloroxybacteria, and eukaryotic alga such as Euglenids, Pyrrophyta (also known as dinoflagellate), *Cryptophyta*, Chrysophyta, *Chlorella*, Phaeophyta, Rhodophyceae, or any combination thereof.

According to the present invention, the Cyanobacteria can be *Gloeocapsa, Chroococcus*, or *Nostoc*, but it is not limited thereto. Besides, the Chrysophyta can be planktonic alga, such as Bacillariophyceae, but it is not limited thereto.

According to the present invention, the *Nostoc* can be *Nostoc commune* or *Nostoc flagelliforme*, which are also cyanbacteria belonging to *Nostoc* genus and are edible.

According to the present invention, the *Chlorella* can be Ulvaceae, Caulerpaceae, or a combination thereof. Among them, the Ulvaceae can be *Ulva* (also known as sea lettuce), Enteromorpha, Enteromorpha clathrate, *Ulva compressa, Ulva* conglobate, *Ulva fasciata*, Enteromorpha intestinalis, *Ulva linza, Ulva lactuca* L., *Ulva* reticulate, *Ulva rigida, Ulva japonica*, but it is not limited thereto. Among them, the Caulerpaceae can be *Caulerpa* lentillifera (also known as sea grapes).

According to the present invention, the Phaeophyta can be *Laminaria japonica, Saccharina japonica, Durvillaea Antarctica*, Cladosiphon okamuranus, or *Undaria pinnatifida*, but it is not limited thereto.

Preferably, the Rhodophyceae can be Sarcodia, *Porphyra*, Gelidium or Solieriaceae, but it is not limited thereto.

Preferably, the natural bio-reactor mixes with and immerses in the mineral nutrient element precursor solution with a specific ratio. Said specific ratio depends on different species of natural bio-reactors, due to the different anti-oxidative abilities provided by the different natural bio-reactors. In some embodiments, a weight of the natural bio-reactor can be 1 kg to 5 kg. More preferably, a weight of the natural bio-reactor can be 1.2 kg to 3.6 kg.

According to the present invention, a required reaction time depends on the species of the natural bio-reactor and the concentration of mineral nutrient element precursor solution.

Preferably, the reaction time may be 1 hour to 240 hours. For example it can be 1 hour to 200 hours. In some embodiments, the reaction time may be 6 hours to 240 hours. Preferably, the reaction time is 10 hours to 60 hours. For example, it can be 10 hours to 15 hours, 20 hours to 28 hours, or 40 hours to 52 hours. More preferably, the reaction time may be 12 hours to 24 hours.

Preferably, said Step (2) reacts under a pH value of pH 3.8 to pH 8. For example, it can be pH 5 to pH 6.5, pH 5.2 to pH 6, or pH 3.8 to pH 4.4. More preferably, said Step (2) reacts under pH 6 to pH 8.

Preferably, the method for producing biomimetic nutrient mixture via biomimicry further comprises: Step (3) removing the nutrient solution from the biomimetic nutrient mixture to obtain the mineral nutrient element.

Preferably, the means of removing may be decantation, filtration, etc. More preferably, the means of removing is filtration. Preferably, the Step (3) is removing the nutrient solution from the biomimetic nutrient mixture by a 20 mesh to 100 mesh sieve to obtain the mineral nutrient element. The removed nutrient solution can be used to react with the natural bio-reactor for another reaction. More preferably, the 20 mesh to 100 mesh sieve is a 50 mesh sieve.

According to the present invention, the collected mineral nutrient element can be used for continuous algal cultivation, producing liquid fertilizer, or adding to functional food after drying.

Preferably, said Step (2) comprises:

Step (2-1) reacting the mineral nutrient element precursor solution with a natural bio-reactor as a first reaction to obtain a first biomimetic nutrient mixture, wherein the first biomimetic nutrient mixture comprises a first mineral nutrient element and a first nutrient solution, wherein the first nutrient solution comprises a remaining nutrient element precursor after the first reaction; and Step (2-2) reacting the first nutrient solution with a natural bio-reactor as a second reaction to obtain a second biomimetic nutrient mixture, wherein the second biomimetic nutrient mixture comprises a second mineral nutrient element and a second nutrient solution, wherein the mineral nutrient element comprises the first mineral nutrient element and the second mineral nutrient element, wherein the second nutrient solution comprises a remaining nutrient element precursor after the second reaction. More preferably, said Step (2-2) can be repeated for more than once. For example, when the Step (2-2) is repeated once, it means in the Step (2), three fresh natural bio-reactors are used for three reactions, respectively. Specifically, for the biomimetic nutrient mixture subjected to the third reaction, the Step (2-2) comprises: reacting the first nutrient solution with a natural bio-reactor as a second reaction, which means reacting the remaining nutrient element precursor after the first reaction in the first nutrient solution with a fresh natural bio-reactor to obtain the second biomimetic nutrient mixture, and the second biomimetic nutrient mixture comprises the second mineral nutrient element and the second nutrient solution; and then reacting the second nutrient solution with a natural bio-reactor as a third reaction, which means reacting the remaining nutrient element precursor after the second reaction in the second nutrient solution with a fresh natural bio-reactor to obtain the third biomimetic nutrient mixture, wherein the third biomimetic nutrient mixture comprises a third mineral nutrient element and a third nutrient solution.

Said method produces the mineral nutrient element beneficial for organism growth by utilizing the biomimicry with multiple continuous circulations for the reaction in said Step (2-2) without using expensive equipment. Therefore, it is in favor of massive production and has the potential of commercial practice. In addition, this preparation method can achieve carbon-negative and nitrogen-negative emission. The producing process has the advantages of being simple, safe, efficient, low cost, non-toxic, degradable, reusable and recyclable. Besides, using the nutrient solution, which is a by-product, as a raw material to react with the natural bio-reactor is a reaction having 100% atom economy.

According to the present invention, a diffusion reaction occurs at the beginning when the mineral nutrient element precursor solution reacts with the natural bio-reactor in the Step (2). Specifically, the mineral nutrient element precursor solution, the nutrient solution, the first nutrient solution, or the second nutrient solution mixes and contacts with the natural bio-reactor or immerses in the natural bio-reactor for a period of time. The natural bio-reactor has a cell wall containing micrometer-sized pores, so that the high concentrated colloidal particles comprising metal salt or metalloid salt in the mineral nutrient element precursor solution, the nutrient solution, the first nutrient solution, or the second nutrient solution diffuse into the natural bio-reactor, which is relatively low concentrated colloidal particles comprising metal salt or metalloid salt, during the mixing or immersing process.

Preferably, the reaction time may be 1 hour to 48 hours. Preferably, the reaction time is 6 hours to 24 hours. More preferably, the reaction time is 6 hours to 12 hours. The reaction time can be adjusted according to the species of alga or cyanobacteria and the concentration of mineral nutrient element precursor solution, the first nutrient solution, or the second nutrient solution.

According to the present invention, the obtained mineral nutrient element is in the form of colloidal particles with the particle size from 1 nanometer (nm) to 600 nm. With this size, the colloidal particles can diffuse into the cells of alga or cyanobacteria to provide the mineral nutrient element. That is to say, the colloid particle can exist in the biomimetic nutrient mixture or the natural bio-reactor. Preferably, a particle size of the colloidal particle is 50 nm to 550 nm. More preferably, a particle size of the colloidal particle is 75 nm to 500 nm.

According to the present invention, the reaction rate can be adjusted according to the species of alga or cyanobacteria and the type of nutrient solution, so that the colloidal particles comprising metal or metalloid meeting various size requirements can be obtained.

According to the present invention, there is no specific limitation of the reaction temperature of the Step (2). As long as the steps can be proceeded, the temperature is applicable in the present invention. Since the reaction temperature is one of the factors which affect the reaction rate, if the reaction temperature is further controlled, the reaction in each step can be proceeded more evenly and the quality of the final product, the mineral nutrient element, can be promoted. Preferably, the reaction temperature of the Step (2) is 2° C. to 40° C. Preferably, the reaction temperature of the Step (2) is 9° C. to 40° C. More preferably, the reaction temperature of the Step (2) is 20° C. to 30° C.

The advantage of the present invention is that by using biomimicry, the auto-synthesized natural anti-oxidative component during the photosynthesis can be used as a reducing agent, while the salt compound goes through the reduction reaction under room temperature to produce the nutrient elements having high biological activity. The mineral nutrient element can be provided without an extraction process or addition of accessory ingredients. If the multiple continuous circulations are further adopted, the resource of the material can further be fully utilized, so the cost is reduced and the 100% atom economy is achieved. Besides, the quality of the product and the efficiency of the production are promoted, so that the production system has the best effectiveness and the benefits such as high efficiency, low waste and low cost. Since the process has the effect of carbon negative and the nitrogen negative emission, it has several indispensable advantages and commercial potential.

BRIEF DESCRIPTION OF THE DRAWINGS

FIG. 2 is a flow chart of the method for producing biomimetic nutrient mixture via biomimicry of the present invention:

DETAILED DESCRIPTION OF THE PREFERRED EMBODIMENTS

Hereinafter, one skilled in the arts can easily realize the advantages and effects of the instant disclosure from the following examples. Therefore, it should be understood that the descriptions proposed herein are just preferable examples for the purpose of illustrations only, not intended to limit the scope of the disclosure. Various modifications and variations could be made in order to practice or apply the instant disclosure without departing from the spirit and scope of the disclosure.

In the following examples, all the reagents were reagent grade and used as purchased from Acros Organics without further purification. The water was distilled or deionized. Each Example was performed according to the method for producing biomimetic nutrient mixture shown in FIG. 1. Instruments:

1. UV-Vis spectrophotometer: SPECORD 200 Plus manufactured by Analytik Jena;

2. Zeta-potential and particle size analyzer: Litesizer 500 manufactured by Anton Paar;

3. Microprocessor pH/ORP meter: SP-2500 combined with anti HF electrode manufactured by SUNTEX; and 4. Precision balance: PS 3500.R2.M manufactured by Radwag.

In the following Examples and Comparative Example, 1.2 kg to 3.6 kg cyanobacteria or alga (*Chlorella*, Phaeophyta, Rhodophyceae) were added to a solution of 0 M to 0.5 salt, chloride, or oxide of metal or metalloid to give a mixture and then the mixture was cultured under a condition of 9° C. to 40° C. and a pH ranging from 4 to 8 for 6 hours to 200 hours. During the culturing period, water was provided by intermittent water circulation without adding fresh water, therefore the concentration of the mineral nutrient element precursor solution was not affected.

Example 1

Figure 1:
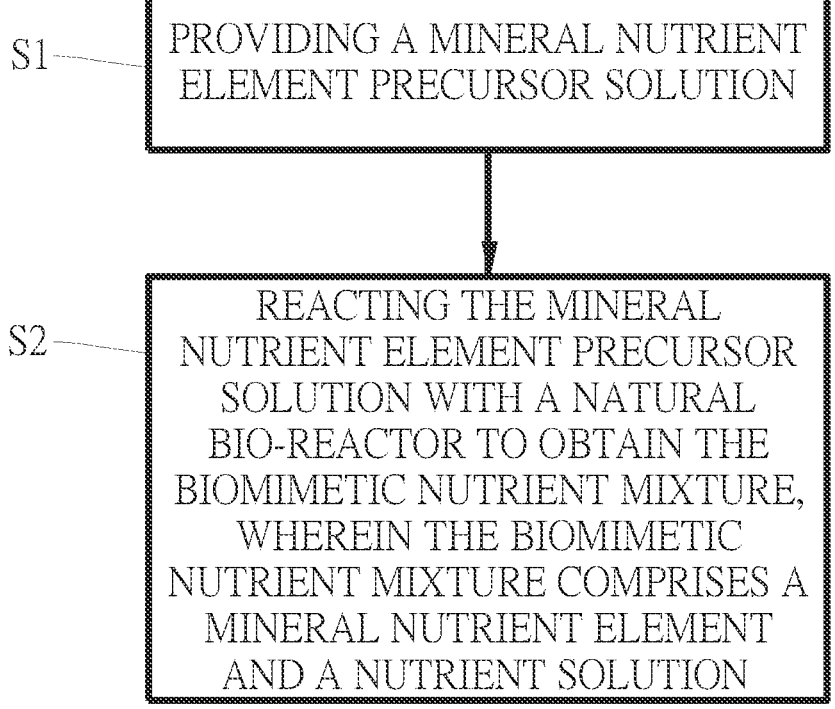
FIG. 1 is a flow chart of the method for producing biomimetic nutrient mixture via biomimicry of the Examples 1 to 5 of the present invention.

First, according to Step S1 shown in FIG. 1, a mineral nutrient element precursor solution was provided. Specifically, the mineral nutrient element precursor solution in the present example is selenium oxide solution.

According to Step S2 shown in FIG. 1, the selenium oxide solution was then reacted with a natural bio-reactor to obtain a biomimetic nutrient mixture, wherein the biomimetic nutrient mixture comprises a mineral nutrient element and a nutrient solution. In the example, the natural bio-reactor was 1.5 kg *Nostoc commune*. Specifically, 100 mL 0.1M selenium oxide solution was added to a 30 L culturing pool containing 1.5 kg *Nostoc commune*. Besides, a weight ratio of the algae and the water was 1:4, which enabled the selenium oxide solution to react with *Nostoc commune* under room temperature to obtain the biomimetic nutrient mixture, wherein the biomimetic nutrient mixture comprises a mineral nutrient element and a nutrient solution. Said mineral nutrient element is Se.

During the incubation period, the intermittent water circulation was adopted to stir the algae, therefore the algae can be evenly dispersed in the algae solution and be exposed to light for continuous photosynthesis and fully reaction. The total reaction time is 12 hours of incubation period.

Figure 3:
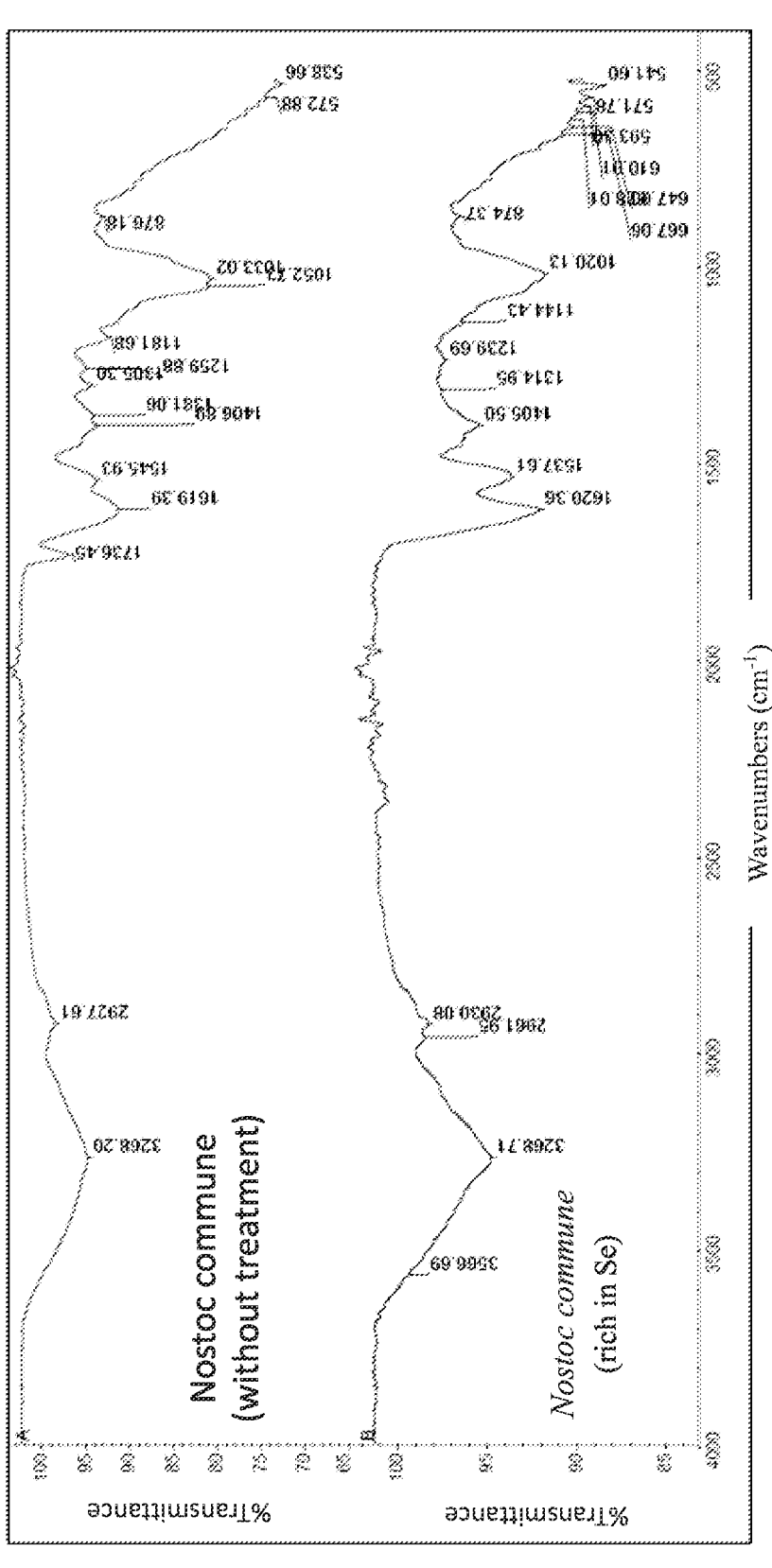
FIG. 3 is a FTIR spectrum of the biomimetic nutrient mixture produced by the examples of the present invention.

In this example, the present invention produces a massive amount of mineral nutrient element: Se element. Thus, it can be observed that compared to water-culturing group (control group), *Nostoc commune* was healthy and stout. This elaborates that *Nostoc commune* can survive in a solution comprising Se element. During incubation, *Nostoc commune* was filtered to obtain *Nostoc commune* rich in Se and a nutrient solution rich in Se. The *Nostoc commune* rich in Se was washed and the water remaining on its surface was dropped, followed by weighting, and it was found that the weight of *Nostoc commune* was 38.89% more compared to the control group and was 56.25% more compared to the weight measured before processing the method of the present invention. In addition, as shown in FIG. 3, the biomimetic nutrient mixture rich in Se shows a slightly difference in a FTIR spectrum, which elaborates that Se nanoparticle was absorbed on the surface of *Nostoc commune*. Besides, a pH value of the nutrient solution of the present example was around 6.3.

Comparative Example 1

Comparative Example 1 was similar to Example 1, except the material of the Comparative Example 1 was not the mineral nutrient element precursor solution but a solution comprising synthesized Se colloid particles, which were obtained after adding 100 mg ascorbic acid to 5 L of 0.1 M sodium selenite for reaction. The present Comparative Example is used to confirm whether the intermittent water circulation provides the nutrient solution to *Nostoc commune* circularly until the synthesized Se colloid particles in the aqueous solution comprising synthesized Se colloid particles were consumed completely.

Since there was a massive amount of mineral nutrient element: Se element, it can be observed that compared to water-culturing group (control group), the *Nostoc commune* was healthy and stout. This elaborates that *Nostoc commune* can survive in a solution comprising Se element. During incubating, *Nostoc commune* was filtered to obtain *Nostoc commune* rich in Se and a nutrient solution rich in Se. The *Nostoc commune* rich in Se was washed and the water remaining on its surface was dropped, followed by weighting, and it was found the weight of *Nostoc commune* was 34.44% more compared to the control group and was 51.25% more compared to the weight measured before providing the aqueous solution comprising synthesized Se colloid particles. Based on the present Comparative Example, it can be proved that *Nostoc commune* can survive in a solution comprising synthesized Se colloid particles, *Nostoc commune* grows better compared to the control group, and the synthesized Se colloid particles can diffuse into *Nostoc commune* in the aqueous solution. This elaborates that with the intermittent water circulation, the nutrient solution can be provided to *Nostoc commune* unlimited times to produce *Nostoc commune* rich in Se continuously until the synthesized Se colloid particles in the aqueous solution comprising synthesized Se colloid particles were consumed completely. A pH value of the nutrient solution of the present was around 5.1. Compared to Example 1, it can be found that the mineral nutrient element precursor solution, which is the material used in Example 1, enhances organism growth better than the colloidal particles does.

In addition, the present Comparative Example proves that the intermittent water circulation can provide the nutrient solution to *Nostoc commune* circularly until the synthesized Se colloid particles in the aqueous solution comprising synthesized Se colloid particles are consumed completely. That is to say, as the method of Comparative Example 1 corresponds to the multiple reaction steps as shown in the FIG. 2 of the present invention, the nutrient solution can be circulated and provided to *Nostoc commune* with unlimited circulating times. Therefore, it is also applicable to add the fresh *Nostoc commune* multiple times for multiple reactions. The reaction can occur multiple times as described in the Step 2-1 and Step 2-2 shown in FIG. 2, which produce the mineral nutrient element continuously and the algae rich in mineral nutrient element can be obtained.

Example 2

Example 2 was similar to Example 1, and the differences were: the mineral nutrient element precursor solution was 100 mL silver nitrate solution with a concentration of 0.1M, the natural bio-reactor was 2 kg *Porphyra*, and the culturing period was 12 hours. Therefore, the obtained mineral nutrient element in the present example was Ag.

Since a massive amount of mineral nutrient element, Ag element, was produced, it can be observed that compared to water-culturing group (control group), *Porphyra* was healthy and stout. This elaborates that *Porphyra* can survive in a solution comprising Ag element. During incubating, *Porphyra* was filtered to obtain *Porphyra* rich in Ag and a nutrient solution rich in Ag. The *Porphyra* rich in Ag was washed and the water remaining on its surface was dropped followed by weighting, and it was found that the weight of *Porphyra* was 37.04% more compared to the control group and was 54.17% more compared to the weight measured before processing the method of the present invention. Besides, a pH value of the nutrient solution of the present example was around 5.6.

Example 3

Example 3 was similar to Example 1, and the differences were: the mineral nutrient element precursor solution was 100 mL copper sulphate solution with a concentration of 0.2 M, the natural bio-reactor was 2 kg Gelidium, and the culturing period was 24 hours. Therefore, the obtained mineral nutrient element in the present example was Cu.

Since a massive amount of mineral nutrient element, Cu element, was produced, it can be observed that compared to water-culturing group (control group), Gelidium was healthy and stout. This elaborates that Gelidium can survive in a solution comprising Cu element. During incubating, Gelidium was filtered to obtain Gelidium rich in Cu and a nutrient solution rich in Cu. The Gelidium rich in Cu was washed and the water remaining on its surface was dropped followed by weighting and it was found that the weight of Gelidium was 28.15% more compared to the control group and was 44.17% more compared to the weight measured before processing the method of the present invention. Besides, a pH value of the nutrient solution of the present example was around 5.4.

Example 4

Example 4 was similar to Example 1, and the differences were: the mineral nutrient element precursor solution was 50 mL zinc nitrate solution with a concentration of 0.3 M, the natural bio-reactor was 1.5 kg *Undaria pinnatifida*, and the culturing period was 24 hours. Therefore, the obtained mineral nutrient element in the present example was Zn.

Since a massive amount of mineral nutrient element, Zn element, was produced, it can be observed that compared to water-culturing group (control group), *Undaria pinnatifida* was healthy and stout. This elaborates that *Undaria pinnatifida* can survive in a solution comprising Zn element. During incubating, *Undaria pinnatifida* was filtered to obtain *Undaria pinnatifida* rich in Zn and a nutrient solution rich in Zn. The *Undaria pinnatifida* rich in Zn was washed and the water remaining on its surface was dropped followed by weighting and it was found that the weight of *Undaria pinnatifida* was 0.74% more compared to the control group and was 13.33% more compared to the weight measured before processing the method of the present invention. Besides, a pH value of the nutrient solution of the present example was around 4.2.

Example 5

Example 5 was similar to Example 1, and the differences were: the mineral nutrient element precursor solution was 150 mL chloroauric acid solution with a concentration of 0.05 M, the natural bio-reactor was 3 kg *Nostoc commune*, and the culturing period was 48 hours. Therefore, the obtained mineral nutrient element in the present example was Au.

Since a massive amount of mineral nutrient element, Au element, was produced, it can be observed that compared to water-culturing group (control group), *Nostoc commune* was healthy and stout. This elaborates that *Nostoc commune* can survive in a solution comprising Au element. During incubating, *Nostoc commune* was filtered to obtain *Nostoc commune* rich in Au and a nutrient solution rich in Au. The *Nostoc commune* rich in Au was washed and the water remaining on its surface was dropped followed by weighting and it was found that the weight of *Nostoc commune* was 22.96% more compared to the control group and was 38.33% more compared to the weight measured before processing the method of the present invention. Besides, a pH value of the nutrient solution of the present example was around 4.7.

Test 1: Analysis of pH Value

The pH meter was used for analyzing the pH value of the biomimetic nutrient mixture containing colloid particles of Examples 1 to 5 and the aqueous solution comprising synthesized colloid particles of Comparative Example 1. The results are shown in the following Table 1:

TABLE 1

The pH value of the biomimetic nutrient mixture
containing colloid particles of Examples 1 to 5 and
the aqueous solution comprising synthesized
colloid particles of Comparative Example 1

| group | Example 1 | Example 2 | Example 3 | Example 4 | Example 5 | Comparative Example1 |
|---|---|---|---|---|---|---|
| element | Se | Ag | Cu | Zn | Au | Se |
| pH value | 6.3 | 5.6 | 5.4 | 4.2 | 4.7 | 5.4 |

According to naked-eye observation results, algae can survive and grow well in different pH ranges and different elements in Examples and Comparative Examples. Besides, the weight ratio of algae in different groups increased significantly compared to the control group.

Test 2: Analysis of Optical Properties

The UV-Vis spectrophotometer was used for analyzing the properties of biomimetic nutrient mixture containing colloid particles of Examples 1 to 5 and the aqueous solution comprising synthesized colloidal particles of Comparative Example 1. The properties were analyzed by the significant resonance phenomenon of a light scattering spectroscopy, so-called surface plasmon resonance. The resonance frequency is related to size, shape, material and adjacent substance of the particles. The analysis method was: first, one part of the biomimetic nutrient mixture containing colloid particles or the aqueous solution comprising colloidal nanoparticles was taken, and then an equal volume of deionized water was added into the part of the biomimetic nutrient mixture containing colloid particles or the aqueous solution comprising colloidal nanoparticles and mixed well to make a diluted sample. After that, each of the diluted samples was measured by the UV-Vis spectrophotometer.

Figure 4:
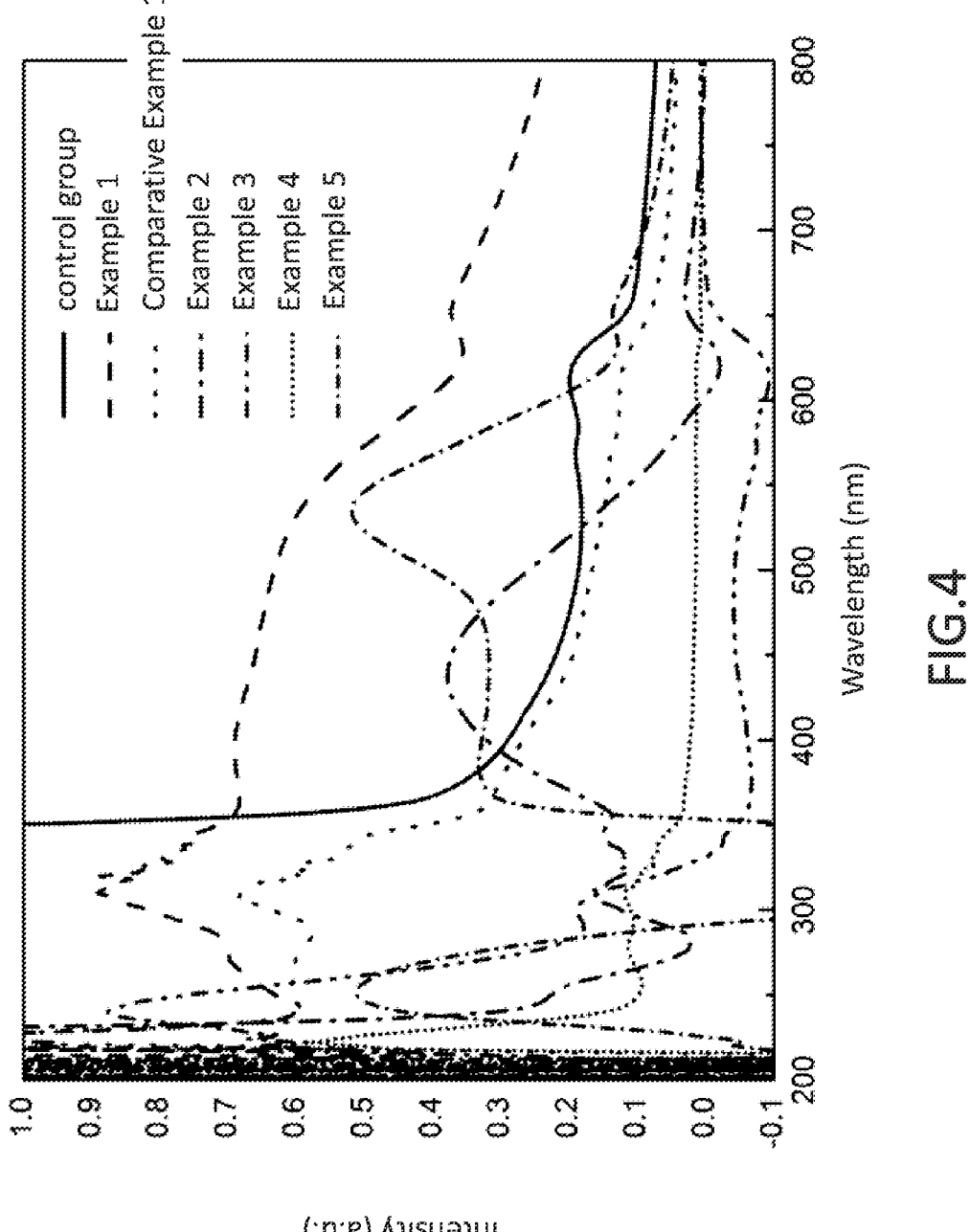
FIG. 4 is a UV-Vis spectrum of the biomimetic nutrient mixture produced by the examples of the present invention.

As shown in FIG. 4, the $\lambda_{max}$ values of Example 1 and Comparative Example 1 were 250 nm to 350 nm, because their mineral nutrient element was Se; the $\lambda_{max}$ value of Example 2 was 400 nm to 500 nm, because its mineral nutrient element was Ag: the $\lambda_{max}$ value of Example 3 was 400 nm to 600 nm, because its mineral nutrient element was Cu; the $\lambda_{max}$ value of Example 4 was 300 nm to 400 nm, because its mineral nutrient element was Zn; the $\lambda_{max}$ value of Example 5 was 500 nm to 600 nm, because its mineral nutrient element was Au.

In addition, the biomimetic nutrient mixture of the present invention is not pure substance, but a nutrient mixture. Thus, there are also other characteristics peaks shown in FIG. 4. For example, the related products of photosynthesis such as flavonoids, indole, polysaccharides, phycobiliproteins, etc. also show characteristics peaks. The absorption peaks of the aforementioned related products of photosynthesis are: 304 nm to 350 nm (flavonoids absorption peak), and around 350 nm (indole absorption peak). For phycobiliproteins (comprising phycoerythrin, phycocyanin, and allophycocyanin), their spectroscopy data shows not only the normal protein absorption peak (280 nm) in UV-visible region (200 nm to 700 nm) but also shows the corresponding absorption peaks, respectively. For example, phycoerythrin has a strong absorption peak at 565 nm; phycocyanin has a strong absorption peak at 620 nm: allophycocyanin has a strong absorption peak at 650 nm.

Test 3: Analysis of Particle Sizes of Biomimetic Nutrient Mixture Containing Colloid Particles Brownian motion is the random motion of suspended particles, such as colloids, resulting from the particles are hit by liquid molecules. Whenever one hit is encountered, the suspended particles change the direction of motion. By the intensity change of the light scattered by the suspended particles, the correlated time can be statistically measured. Therefore, according to the Stokes-Einstein diffusion coefficient equation, the diffusion coefficient of the suspended particles can be obtained, the particle size of each particle can be obtained, the diameter distribution diagram of all particles can be obtained, and a polydispersity index (PDI) can be calculated. The particle size distribution of each of the biomimetic nutrient mixtures containing colloid particles of Examples 1 to 5 and the aqueous solution comprising synthesized colloid particles of Comparative Example 1 was analyzed with the Zeta-potential and a particle size analyzer. As shown in following Table 2, the particle size distributed from 100 nm to 400 nm. Since the size of algae ranges from 1 μm to 2 μm of the smallest algae to 60 meters of the biggest algae, the colloid particles can diffuse into the algae and provide the mineral nutrient element thereto. Besides, the PDI values of Examples 1 to 5 range from 0.2 to 0.5.

TABLE 2

The Particle Sizes Analysis Results of each Example and Comparative Example

| group | Example 1 | Example 2 | Example 3 | Example 4 | Example 5 | Comparative Example1 |
|---|---|---|---|---|---|---|
| element | Se | Ag | Cu | Zn | Au | Se |
| Size (nm) | 177 | 137 | 178 | 158 | 235 | 307 |
| PDI | 0.306 | 0.415 | 0.464 | 0.382 | 0.281 | 0.417 |

Test 4 DPPH Free Radical Scavenging Assay

The DPPH free radical scavenging ability of each of the biomimetic nutrient mixtures containing colloid particles of Examples 1, 4 and 5 was measured. 7.2 ppm DPPH solution (in methanol) was prepared by mixing DPPH (2,2-diphenyl-1-picrylhydrazyl, Tokyo Chemical Industry, D4313, CAS No.: 1898-66-4) with methanol evenly. 0.1 mL test specimen (biomimetic nutrient mixture containing colloid particles) was mixed with 10 mL aforementioned DPPH solution evenly for 35 minutes, and was centrifuged at 8000 rpm for 10 minutes. The supernatant was used for Spectral measurement. The reduced extent of DPPH absorbance at 517 nm was utilized for calculating the free radical scavenging ability.

Figure 5:
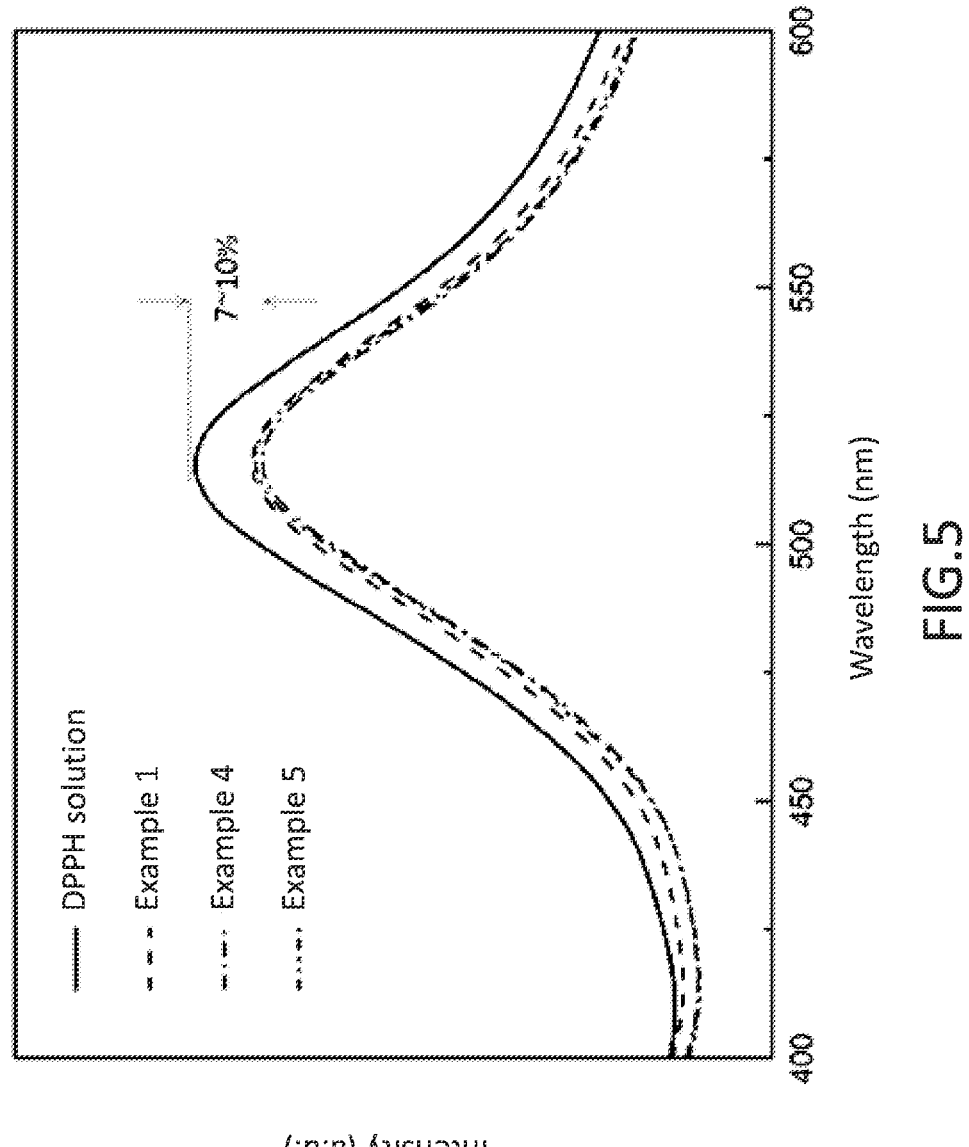
FIG. 5 is DPPH free radical scavenging ability of the biomimetic nutrient mixture produced by the Examples 1, 4 and 5 of the present invention.

As shown in FIG. 5, the absorbance at 517 nm of Examples 1, 4 and 5 was lower than the DPPH solution. DPPH methanol solution has higher absorbance at 517 nm and its absorbance reduces once DPPH was reduced by an antioxidant. The lower the absorbance, the stronger the antioxidant ability. After calculation, the biomimetic nutrient mixtures containing colloid particles of Examples 1, 4 and 5 scavenge around 7% to 10% free radicals. Therefore, the mineral nutrient element of the present invention has high biological activity such as high anti-oxidative ability.

To sum up, the present invention utilizes biomimicry which auto-synthesizes natural anti-oxidative component during the photosynthesis that can be used as a reducing agent, while the salt compound goes through the reduction reaction under room temperature to produce the nutrient elements having high biological activity. The mineral nutrient element, which enhances the growth of organisms, such as human body, animals or plants, can be provided without an extraction process or addition of accessory ingredients. If the multiple continuous circulations are further adopted, the material can further be fully utilized, the cost can be reduced, and the 100% atom economy can be achieved. This promotes the quality of the product and production efficiency.

What is claimed is:

1. A method for producing a biomimetic nutrient mixture via biomimicry, comprising:
Step (1) providing a mineral nutrient element precursor solution, wherein the mineral nutrient element precursor solution is selenium oxide solution, and a mineral nutrient element precursor in the mineral nutrient element precursor solution is selenium oxide; and
Step (2) mixing and reacting the mineral nutrient element precursor solution with a natural bio-reactor for 12 hours to 24 hours with intermittent water circulation to obtain the biomimetic nutrient mixture, wherein
the natural bio-reactor is an organism comprising *Nostoc commune,*
a molar concentration of the mineral nutrient element precursor in a mixture obtained by mixing the mineral nutrient element precursor solution and the natural bio-reactor is 1.25 mM to 6.25 mM,
a weight ratio of selenium oxide and the natural bio-reactor is 1:400 to 1:10000, and
the biomimetic nutrient mixture comprises a mineral nutrient element and a nutrient solution, and the mineral nutrient element is Se element.

2. The method according to claim 1, wherein the mineral nutrient element is in a form of colloid particle.

3. The method according to claim 2, wherein a size of the colloid particle is 1 nanometer (nm) to 600 nm.

4. The method according to claim 1, wherein a reaction temperature of the Step (2) is 2° C. to 40° C.

5. The method according to claim 1, wherein a reaction pH value of the Step (2) is pH3.8 to pH8.

6. The method according to claim 1, further comprising:
Step (3) removing the nutrient solution from the biomimetic nutrient mixture to obtain the mineral nutrient element.

7. The method according to claim 1, wherein Step (2) comprises:
Step (2-1) reacting the mineral nutrient element precursor solution with a natural bio-reactor as a first reaction to obtain a first biomimetic nutrient mixture, wherein the first biomimetic nutrient mixture comprises a first mineral nutrient element and a first nutrient solution, and the first mineral nutrient element is Se element; and
Step (2-2) reacting the first nutrient solution with another natural bio-reactor as a second reaction to obtain a second biomimetic nutrient mixture, wherein the second biomimetic nutrient mixture comprises a second mineral nutrient element and a second nutrient solution, and the second mineral nutrient element is Se element, wherein the mineral nutrient element comprises the first mineral nutrient element and the second mineral nutrient element.

8. The method according to claim 2, wherein Step (2) comprises:

Step (2-1) reacting the mineral nutrient element precursor solution with a natural bio-reactor as a first reaction to obtain a first biomimetic nutrient mixture, wherein the first biomimetic nutrient mixture comprises a first mineral nutrient element and a first nutrient solution, and the first mineral nutrient element is Se element; and
Step (2-2) reacting the first nutrient solution with another natural bio-reactor as a second reaction to obtain a second biomimetic nutrient mixture, wherein the second biomimetic nutrient mixture comprises a second mineral nutrient element and a second nutrient solution, and the second mineral nutrient element is Se element, wherein the mineral nutrient element comprises the first mineral nutrient element and the second mineral nutrient element.

9. The method according to claim 3, wherein Step (2) comprises:
Step (2-1) reacting the mineral nutrient element precursor solution with a natural bio-reactor as a first reaction to obtain a first biomimetic nutrient mixture, wherein the first biomimetic nutrient mixture comprises a first mineral nutrient element and a first nutrient solution, and the first mineral nutrient element is Se element; and
Step (2-2) reacting the first nutrient solution with another natural bio-reactor as a second reaction to obtain a second biomimetic nutrient mixture, wherein the second biomimetic nutrient mixture comprises a second mineral nutrient element and a second nutrient solution, and the second mineral nutrient element is Se element, wherein the mineral nutrient element comprises the first mineral nutrient element and the second mineral nutrient element.

10. The method according to claim 4, wherein Step (2) comprises:
Step (2-1) reacting the mineral nutrient element precursor solution with a natural bio-reactor as a first reaction to obtain a first biomimetic nutrient mixture, wherein the first biomimetic nutrient mixture comprises a first mineral nutrient element and a first nutrient solution, and the first mineral nutrient element is Se element; and
Step (2-2) reacting the first nutrient solution with another natural bio-reactor as a second reaction to obtain a second biomimetic nutrient mixture, wherein the second biomimetic nutrient mixture comprises a second mineral nutrient element and a second nutrient solution, and the second mineral nutrient element is Se element, wherein the mineral nutrient element comprises the first mineral nutrient element and the second mineral nutrient element.

11. The method according to claim 5, wherein Step (2) comprises:
Step (2-1) reacting the mineral nutrient element precursor solution with a natural bio-reactor as a first reaction to obtain a first biomimetic nutrient mixture, wherein the first biomimetic nutrient mixture comprises a first mineral nutrient element and a first nutrient solution, and the first mineral nutrient element is Se element; and
Step (2-2) reacting the first nutrient solution with another natural bio-reactor as a second reaction to obtain a second biomimetic nutrient mixture, wherein the second biomimetic nutrient mixture comprises a second mineral nutrient element and a second nutrient solution, and the second mineral nutrient element is Se element, wherein the mineral nutrient element comprises the first mineral nutrient element and the second mineral nutrient element.

12. The method according to claim 6, wherein Step (2) comprises:

Step (2-1) reacting the mineral nutrient element precursor solution with a natural bio-reactor as a first reaction to obtain a first biomimetic nutrient mixture, wherein the first biomimetic nutrient mixture comprises a first mineral nutrient element and a first nutrient solution, and the first mineral nutrient element is Se element; and Step (2-2) reacting the first nutrient solution with another natural bio-reactor as a second reaction to obtain a second biomimetic nutrient mixture, wherein the second biomimetic nutrient mixture comprises a second mineral nutrient element and a second nutrient solution, and the second mineral nutrient element is Se element, wherein the mineral nutrient element comprises the first mineral nutrient element and the second mineral nutrient element.

* * * * *